United States Patent
Van Dun

(10) Patent No.: US 10,174,370 B2
(45) Date of Patent: Jan. 8, 2019

(54) METHOD FOR ANALYZING MATERNAL DNA IN LARGE PLANT POPULATIONS

(71) Applicant: Rijk Zwaan Zaadteelt en Zaadhandel B.V., De Lier (NL)

(72) Inventor: Cornelis Maria Petrus Van Dun, Roosendaal (NL)

(73) Assignee: RIJK ZWAAN ZAADTEELT EN ZAADHANDEL B.V., De Lier (NL)

( * ) Notice: Subject to any disclaimer, the term of this patent is extended or adjusted under 35 U.S.C. 154(b) by 285 days.

(21) Appl. No.: 14/562,428

(22) Filed: Dec. 5, 2014

(65) Prior Publication Data

US 2015/0126380 A1    May 7, 2015

Related U.S. Application Data

(63) Continuation-in-part of application No. PCT/EP2013/061712, filed on Jun. 6, 2013.

(30) Foreign Application Priority Data

Jun. 7, 2012  (EP) .................................. 12171151

(51) Int. Cl.
| | | |
|---|---|---|
| *C12Q 1/68* | (2018.01) | |
| *C12Q 1/6874* | (2018.01) | |
| *A01H 1/04* | (2006.01) | |
| *C12Q 1/6806* | (2018.01) | |
| *C12Q 1/6895* | (2018.01) | |
| *C12N 15/10* | (2006.01) | |

(52) U.S. Cl.
CPC ............ *C12Q 1/6874* (2013.01); *A01H 1/04* (2013.01); *C12N 15/1003* (2013.01); *C12Q 1/6806* (2013.01); *C12Q 1/6895* (2013.01); *C12Q 2600/13* (2013.01)

(58) Field of Classification Search
None
See application file for complete search history.

(56) References Cited

U.S. PATENT DOCUMENTS

| | | | | |
|---|---|---|---|---|
| 6,107,051 A | * | 8/2000 | Job ...................... | C07K 14/415 435/7.92 |
| 2007/0204366 A1 | * | 8/2007 | Deppermann ........... | A01H 1/02 800/278 |
| 2013/0210006 A1 | * | 8/2013 | Rapier ..................... | C12Q 1/24 435/6.11 |

FOREIGN PATENT DOCUMENTS

| | | |
|---|---|---|
| WO | WO 2007/093448 | 8/2007 |
| WO | WO 2011/119763 * | 9/2011 |
| WO | 2014/195199 A1 | 12/2014 |

OTHER PUBLICATIONS

Chunwongse (Theor Appl Genet 1993 86:694-698).*
Dean (Molecular Plant vol. 4 No. 6 pp. 1074-1091 Nov. 2011).*
Khri bin Mardi (Removing the Seed Coats from Germinated Bean Sprouts Dec. 1, 2002 found online at http://www.fftc.agnet.org/library.php?func=view&id=20110717002004&type_id=7 and downloaded Mar. 24, 2017).*
International Search Report and Written Opinion for International application No. PCT/EP2013/061712.
Heymann Eckhard W et al: DNA Fingerprinting Validates Seed Dispersal Curves from Observational Studies in theNeotropical Legume Parkia', PLOS ONE,vol. 7, No. 4, Apr. 2012.
Pang Jin-Song et al: Construction of the seed-coat cDNA microarray and screening . . . , Acta Biochimica et Biophysica Sinica, vol. 36, No. 10, Oct. 2004, pp. 695-700.
Tatineni Satyanarayana et al: In planta distribution of candidatus Liberibacter asiaticus as revealed by . . . , Phytopathology, vol. 98, No. 5, May 2008, pp. 592-599.

* cited by examiner

*Primary Examiner* — Amanda Haney
(74) *Attorney, Agent, or Firm* — Duane Morris LLP; Thomas J. Kowalski; Deborah L. Lu

(57) ABSTRACT

The present invention relates to a non-destructive method for analyzing maternal DNA of a seed. In this method the DNA may be dislodged from the seed coat surface and may be used to collect information on the genome of the maternal parent of the seed. Also, the present invention provides a high throughput DNA analysis system for large plant populations.

13 Claims, 2 Drawing Sheets

METHOD FOR ANALYZING MATERNAL DNA IN LARGE PLANT POPULATIONS

RELATED APPLICATIONS AND/OR INCORPORATION BY REFERENCE

This application is a continuation-in-part application of international patent application Serial No. PCT/EP2013/061712 filed Jun. 6, 2013, which published as PCT Publication No. WO 2013/182646 on Dec. 12, 2013, which claims benefit of European patent application Serial No. 12171151.9 filed Jun. 7, 2012.

The foregoing applications, and all documents cited therein or during their prosecution ("appin cited documents") and all documents cited or referenced in the appin cited documents, and all documents cited or referenced herein ("herein cited documents"), and all documents cited or referenced in herein cited documents, together with any manufacturer's instructions, descriptions, product specifications, and product sheets for any products mentioned herein or in any document incorporated by reference herein, are hereby incorporated herein by reference, and may be employed in the practice of the invention. More specifically, all referenced documents are incorporated by reference to the same extent as if each individual document was specifically and individually indicated to be incorporated by reference.

FIELD OF THE INVENTION

The present invention relates to a method for analyzing maternal DNA of a seed, and use of the method.

BACKGROUND OF THE INVENTION

Plant breeding depends on the efficient exploitation of genetic variation that resides in the germplasm of a particular crop species, and which determines the phenotype of a plant within a specific environment. While this is traditionally done by selection of a combination of desirable traits observed at the phenotypic level, this can increasingly be performed by selection on the basis of molecular markers which are genetically closely linked to the allelic form of a gene which contributes to the expression of a specific trait.

Selection of traits at the phenotypic level is complex for traits that manifest themselves in a recessive way. When one of the parents has one recessive and one dominant allele for a given gene, and the other parent has two dominant alleles for the same gene, the result of crossing of the two parents will be a population in which—in the absence of segregation distortion—half of the individuals carry one recessive allele for that gene. Those individuals can however not be recognised, since the desired recessive trait will not express itself in a heterozygous situation. Only after selfing and analyzing the offspring in the next generation can it be determined which individual was carrying the recessive allele, and hence which individual was heterozygous.

Usually a plant breeder or researcher wishes to proceed as fast as possible by identifying alleles of interest as early as possible in a plant population. In many situations, it is of particular interest to determine the genetic composition of a mother plant that has produced a particular seed. It is therefore an object of the present invention to provide an efficient and non-disruptive method for examining the genome of the maternal parent of a seed.

Techniques to analyze DNA are developing very rapidly, and they are becoming increasingly efficient and sensitive. These highly sensitive DNA analysis methods require only very small amounts of DNA to generate a reliable signal. The research leading to the present invention demonstrated that such low but detectable amounts of DNA are located on the seed coat surface.

A seed coat develops from degenerated ovule integuments, which is maternal tissue. The ploidy of the seed coat of a diploid plant is 2n, and genetically it is identical to the maternal parent of the seed, i.e. the parent on which the seed has originated and developed.

Various techniques exist for analyzing DNA from plants or seeds. They mainly differ from each other in the way biological material is collected, which tissues or plant organs are used therefor, and in which developmental stage sampling is performed. In commercial settings, it is advantageous to obtain genetic material for analysis (e.g. by means of molecular marker analysis or DNA-sequencing) without the necessity to grow the plants throughout their entire life cycle in order to produce seed of the next generation, or preferably even without the need to germinate the seeds and to grow plants altogether. Thus, one would like to collect DNA from a very early developmental stage, without jeopardising the survival and normal further development of the plantlets.

To traditionally obtain genetic information from a seed, either the seed has to be destroyed, damaged, or grown into a plant, after which the seed or plant tissue can be used for DNA extraction. The present invention, however, provides a non-disruptive and non-invasive method to obtain DNA from a seed coat, from which genetic information about the female parent of that seed can be gathered, without impairing the seed's capacity to germinate and to develop into a plant of the next generation.

Traditionally, seeds are germinated and grown into plantlets from which tissue is subsequently collected, at a developmental stage that allows the harvesting of a sufficiently large tissue fragment without causing critical damage to the plantlets. After DNA extraction, identification of the desired individuals takes place through the use of molecular markers. The remaining plants, which can represent a very large part of the sampled population, are identified as being undesired by the breeder for his targeted purpose, on the basis of their lack of one or more specific molecular markers. Such undesired plants will be discarded, as they merely occupy valuable space in the growth facilities.

An alternative method for obtaining DNA from a plantlet may comprise the collection of detached root border cells from germinated seeds (European patent application EP-1984496). Since no plant tissue is needed, the damage to the plantlets is essentially non-existing, and the speed and efficiency of this method is very high, while costs are low. However, this method still requires the germination of seeds in order to collect root border cells from a radicle or root, and this requires growth space.

Alternatively, DNA can be extracted from a seed, which can then be analysed to determine the genotype of the plant that the seed would give rise to, if the seed would be sown. The most common procedure to extract DNA involves crushing, grinding or destruction of the said seed in some other way, making it impossible to still use the particular plant individual that could have grown from that particular seed. An alternative method involves the cutting off of a small part of the seed, including the endosperm (but not including the embryo), by means of e.g. a cutting device or a laser beam, in such a way that the seed still remains viable and can be grown later on. Such methods are e.g. described in European patent application EP2200419, and in WO2011/082316, WO2011/119763, WO2011/163326 and WO2011/163362.

These techniques require sophisticated and complex equipment, since seeds need to be positioned in a precise and highly reproducible, consistent manner, and meticulously cut to not critically damage the embryo from which a plant should still develop after the tissue harvesting process. Either method takes a considerable amount of technical and experimental development, optimisation and testing time until reliable and useful results can potentially be achieved routinely for any given plant species.

A particular difficulty is the fact that even the seeds of a single species do not always have the exact same shape, size and weight, e.g. due to genetic and/or environmental variables, and this further complicates the practical application of such automated high-throughput seed chipping methods, even on seeds of a single species. Especially for species with round seeds such automated method is very difficult to standardise and optimise, because the exact position of the embryo inside seeds with such a shape is not predictable. Cutting off random parts of such seeds can easily lead to damage to the embryo and a high death rate among the sampled seeds, which is precisely what one wishes to avoid in a non-destructive method for selecting seeds with desired genotypic variants in order to subsequently grow them into plants.

Because of these differences in ploidy and origin, analysis of seed tissue can yield different results and can be used for various goals, depending on the type of tissue layer that is examined. Examination of a complete seed, or a part thereof containing the endosperm and/or embryo, results in information on the genotype of the plant it can generate. This genotype contains maternal as well as paternal genetic information. A study of a seed coat specifically yields data regarding the genome of the maternal parent from which the seed originates. However, it is technically very difficult to obtain DNA from the seed coat. Physical removal of the seed coat is a very tedious and precise activity, and it yields only a very small amount of tissue. Subsequently, the DNA needs to be extracted from the tissue, after which it can be assayed. Typically the seeds are strongly damaged by the removal of seed coat tissue, and they will usually not be usable anymore, certainly not for commercial purposes.

Citation or identification of any document in this application is not an admission that such document is available as prior art to the present invention.

SUMMARY OF THE INVENTION

In the research leading to the present invention, it was surprisingly found that small amounts of DNA are present at the surface of a seed coat, and that this DNA is identical to the DNA of the maternal parent that produced the seed. This DNA may be dislodged from the seed coat surface by contacting a seed with a fluid, and the fluid subsequently contains the dislodged DNA, which may be analyzed for e.g. specific molecular markers, using sensitive molecular analysis techniques. Importantly, this method is non-destructive, as the seed may be dried after having been in contact with the fluid, and stored without loss of germination capacity and viability. This method thus allows the genetic and molecular analysis of the maternal parent of a seed, without damaging the seed or impairing its ability to germinate.

The invention thus relates to a non-destructive method for analyzing maternal DNA of a seed, which may comprise the steps of contacting a seed with a fluid to dislodge DNA from the seed coat surface, and analyzing the DNA thus dislodged from the seed coat surface.

In the present invention, maternal DNA is obtained from the seed coat surface of plant seeds. The seeds of most plants, including monocotyledons (such as grains), as well as dicotyledons (to which legumes and many vegetables belong), consist of three different layers or components. Each of these parts has its own specific ploidy and developmental origin.

The embryo, which will ultimately develop into a new plant, is diploid (2n), with one maternal and one paternal set of chromosomes. The maternal chromosome set is provided by a haploid egg cell, and the paternal set by a haploid sperm cell, which was transported into the embryo sac when the egg cell was fertilized by a pollen tube.

The endosperm, generally forming a source of nutrients for the developing embryo, is in most cases triploid (3n), with two sets of maternal and one set of paternal chromosomes. It originates when the diploid central cell fuses with a second haploid sperm cell, which was transported into the embryo sac when the egg cell was fertilised by a pollen tube.

The outer layer of the seed is the seed coat or testa. It develops from degenerated maternal ovule integuments and is therefore identical to the maternal 2n genome of the mother, without any contribution from the father's pollen.

The present invention provides an efficient and non-disruptive method for obtaining DNA from a seed coat surface. This DNA is identical to the DNA of the maternal parent of the seed. The DNA thus obtained may be used to collect information on the genome of the maternal parent of a seed. The genome of the maternal parent may comprise both the nuclear genome and the cytoplasmic (organellar) genome of the maternal parent plant.

Accordingly, it is an object of the invention to not encompass within the invention any previously known product, process of making the product, or method of using the product such that Applicants reserve the right and hereby disclose a disclaimer of any previously known product, process, or method. It is further noted that the invention does not intend to encompass within the scope of the invention any product, process, or making of the product or method of using the product, which does not meet the written description and enablement requirements of the USPTO (35 U.S.C. § 112, first paragraph) or the EPO (Article 83 of the EPC), such that Applicants reserve the right and hereby disclose a disclaimer of any previously described product, process of making the product, or method of using the product.

It is noted that in this disclosure and particularly in the claims and/or paragraphs, terms such as "comprises", "comprised", "comprising" and the like can have the meaning attributed to it in U.S. Patent law; e.g., they can mean "includes", "included", "including", and the like; and that terms such as "consisting essentially of" and "consists essentially of" have the meaning ascribed to them in U.S. Patent law, e.g., they allow for elements not explicitly recited, but exclude elements that are found in the prior art or that affect a basic or novel characteristic of the invention.

These and other embodiments are disclosed or are obvious from and encompassed by, the following Detailed Description.

BRIEF DESCRIPTION OF THE DRAWINGS

The following detailed description, given by way of example, but not intended to limit the invention solely to the specific embodiments described, may best be understood in conjunction with the accompanying drawings.

DETAILED DESCRIPTION OF THE INVENTION

Figure 1:
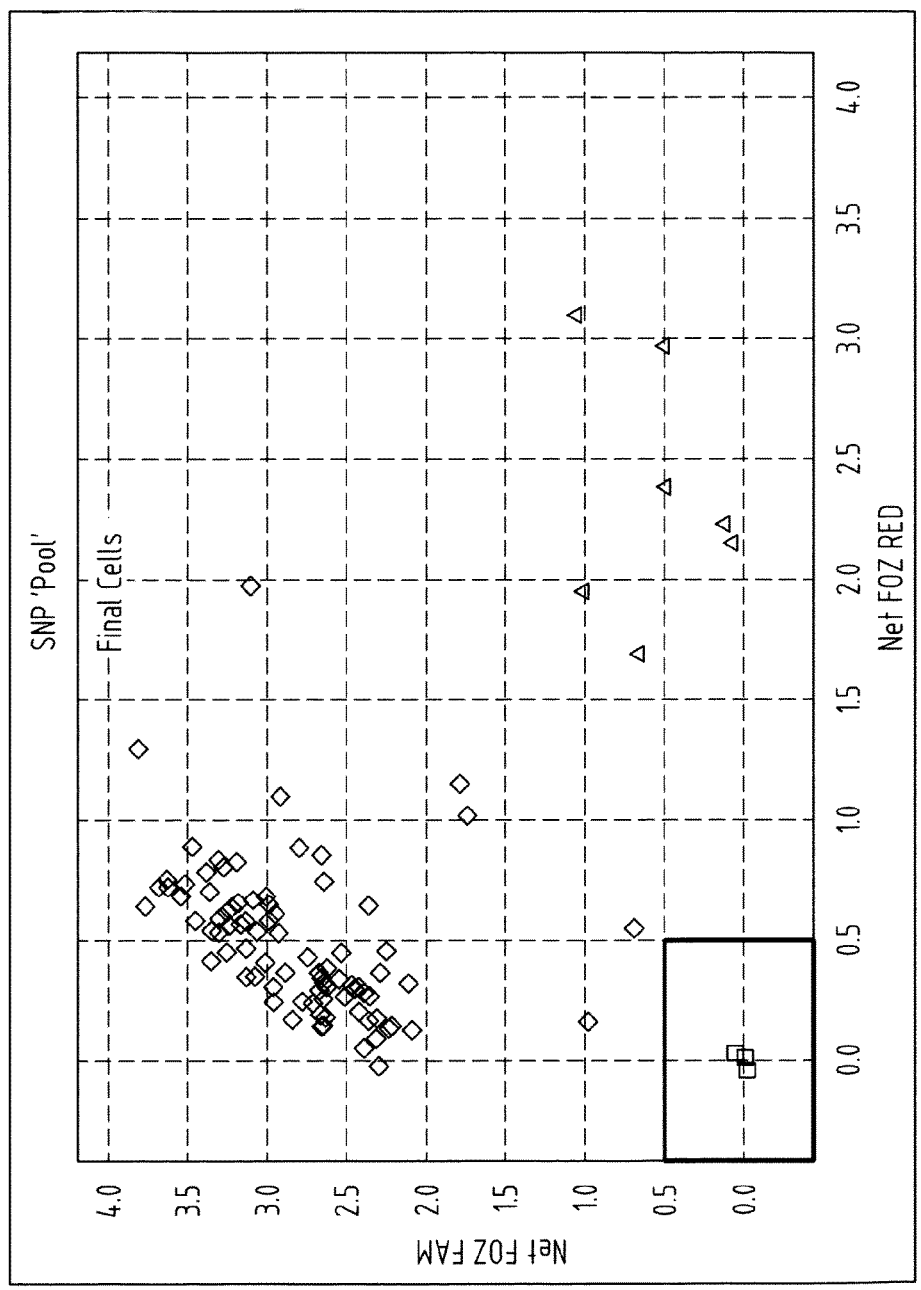
FIG. 1 shows the detection of contaminating fertile Brassica progeny among a batch of male sterile Brassica seeds, by means of a CMS marker detected in seed coat DNA.

Ploidy of a plant, or of a tissue of a plant, is determined by the nuclear chromosome number. Some genes however reside on extranuclear DNA, which may be found in particular cytoplasmic organelles, such as chloroplasts and mitochondria. The cytoplasmic organelles reside in the cytoplasm of a cell, which surrounds the nucleus of the cell. In many cells organelles are present in large numbers, which makes it easy to detect organellar DNA due to the high copy-number of the organellar DNA in such a cell. Cytoplasm with organelles is e.g. present in egg cells, which are the gametes produced by the female parent.

When an egg cell is fertilised by one of the two sperm cells (alternatively named "generative cells") from a father plant that are delivered into the embryo sac by a pollen tube, usually none of the pollen grain's cytoplasm (containing the organelles of the father plant) is transferred along with the sperm nucleus. In nearly all cases organelles are namely entirely absent from the two generative cells, due to an asymmetric distribution of the organelles during the first pollen mitosis that occurs during pollen development. This asymmetric first pollen mitosis leads to the formation of one large vegetative nucleus and one small generative nucleus. Hereby the vegetative cell typically retains all of the microspore's organelles and nearly all of its cytoplasm, while the generative cell typically receives only a very small amount of cytoplasm, and no organelles.

Later in pollen development the generative cell—which resides within the cytoplasm of the vegetative cell—divides again (second pollen mitosis), to give rise to two generative cells. When an egg cell is fertilised by one of these two generative cells from a father plant, this thus leads to a zygote with cytoplasmic organelles that are exclusively maternal in origin, and a nuclear genome consisting of essentially equal contributions from both parents. The father thus only contributes nuclear DNA to the zygote, but no organellar DNA. Consequently, extranuclear DNA inherits exclusively through the maternal parent. This process is known as cytoplasmic inheritance.

Several important genes for plant breeding, among which male sterility genes in several plant species, may be found in the cytoplasm. Cytoplasmic male sterility (CMS) genes may for example only be inherited through a female parent, as illustrated by Example 2.

There are many interesting features that may be determined from analyzing maternal DNA from a seed. Information on the maternal parent of a seed (i.e. on the maternal contribution to a seed's genome) may yield data on the origin of a seed. This type of information is very useful for phylogenetic analysis and other evolutionary studies, or for tracking of dispersed seeds to assess seed movements. For example, in certain areas of research, seeds that are dispersed by birds are being tracked, by comparing the DNA from the seed coats. By identifying which seeds originate from the same mother, the seed movement away from this mother plant (e.g. an individual tree) may be followed, and genetic variability within and between different (e.g. geographically distinct) seed pools may be established (trivet et al. (2005), Mol. Ecol. 14: 3585-3595). However, it is very cumbersome to collect the DNA from the seed coats, as the methods in the state of the art all involve the physical removal of the seed coats from the seeds.

Knowledge of the maternal component of a hybrid genome (in addition to knowledge of the genetic composition of that hybrid genome itself) may also be used to derive information about the genetic identity and genomic properties of the father of the seed, if the identity of the father is unknown.

Commercial seed companies have other reasons to be interested in the possibility to obtain information on the maternal parent of a seed. An important commercial application is the use of the invention in quality control of seeds.

When seeds of commercial plant varieties are produced on a large scale, often many different varieties are produced at the same time and on the same location. Obviously mistakes may occur during that process, and a certain risk of contamination exists. There is a possibility that the wrong parent is used for a certain production, or that the parent that is used still contains undesired genetic variation. Also during harvesting and further processing of the seeds it is possible that mixtures occur. Because seeds are the essential starting material for the grower of a certain crop, it is of the utmost importance that the grower gets exactly what he has ordered and expects to receive from the seed company. Quality control is therefore a crucial duty of a seed company, to ensure that its customers receive seeds of the highest possible quality and uniformity.

In addition, quality control activities absorb a lot of time, space and/or money, depending on the method that is used, and they may significantly delay the market entry of a commercial seed lot. It is therefore of great importance to obtain information on possible impurities as early and as quickly as possible in the process. Impurities in seed batches may arise from different causes. Analysis of maternal nucleic acids may be used to determine whether specific seeds originate from the correct mother plant, and hence whether seed batches are homogenous. Possible problems that may be identified by analyzing the female genotype of a seed are a wrong seed identity, mixing of seed batches that could have occurred at various stages in the seed production process (e.g. planting of the parental lines, fertilisation, harvesting, and bagging of seeds), and non-uniformity or non-homozygosity of the female parent.

Quality control is performed on commercial seed lots to check the identity, purity and uniformity of the produced batches of seed. Quality control may be done in various ways, for example through molecular methods or through in vivo observation of phenotypes of a representative sample of seeds. Either method results in the loss of a certain amount of precious seeds, since the procedures are destructive and the seeds on which they are performed may no longer be marketed. The present invention allows the non-destructive sampling of maternal DNA from seeds, without impairing the viability or germination capacity of the seeds. Thus, the seeds may still be stored, germinated and commercially sold after sampling has occurred. This feature makes the invention particularly suited for quality control purposes. This application is illustrated by Example 4.

Another important application for the specific analysis of maternal DNA of a seed lies in identifying genetic variation in large plant populations. An example is a mutagenised plant population, such as is typically obtained in e.g. a TILLING approach. The analysis of the maternal genome of individual or batched seeds may greatly reduce the time, costs, labour and growth space that is needed for the identification of plant individuals harbouring desired genetic variation. This is illustrated by example 5.

The present invention provides a non-destructive method for analyzing maternal DNA of a seed, which may comprise the steps of contacting a seed with a fluid to dislodge DNA from the seed coat surface, and analyzing the DNA thus dislodged from the seed coat surface. Contacting the seed with the fluid is preferably done in a container which allows easy sampling from the fluid and automation of the sampling process.

According to the invention, DNA from the seed coat surface is obtained in a non-disruptive manner, which may comprise contacting the seed with a fluid. Non-disruptive implies that the seed is not crushed or damaged in any way, such that it retains its capacity to germinate and to generate a plant.

"Maternal DNA of a seed" herein may comprise the genomic DNA of the mother plant that produced the seed. This DNA may be of nuclear and/or cytoplasmic origin, and it allows for example the identification of the mother plant that produced the said seed, and the identification of the maternal contribution to the seed's genome. The maternal DNA may be examined by means of different nucleic acid analysis technologies, preferably using a highly sensitive detection method. Such analysis technologies are well-known to the person skilled in the art.

The contacting between seed and fluid is done by immersing the seed in the fluid, or by floating the seed on the fluid. Optionally, the seed within the fluid may be gently agitated to facilitate the dislodging of the DNA into the fluid. However, this is not always required to obtain seed coat DNA. The seed may also be rinsed with the fluid. The fluid with which the seed is contacted or rinsed is an aqueous solution, such as water or a buffer.

After a short period of time in the fluid or on the fluid, the seed may either be removed from the fluid, or left inside the fluid. The fluid that now contains the seed coat DNA is preferably immediately assayed. A "short period of time" means herein a period of time that is significantly shorter than the time which is required to imbibe the seeds and to irreversibly trigger germination. Suitable times are between 30 seconds and 30 minutes, preferably between 1 and 15 minutes, more preferably between 2 and 5 minutes.

If the seed is removed from the fluid, the seed may be dried and stored. The germination capacity of the seed is not affected by this method if it is removed and dried back immediately after the seed coat DNA has been collected. By using the method of the invention, the analysed seed is thus not damaged and it may, if desired, still be stored, germinated and commercially sold and used afterwards.

The fluid that has been contacted with the seed contains DNA from the seed coat surface. The DNA originates from the maternal parent of the seed. This maternal DNA may be assayed for any genetic information that is desired. The genome (both nuclear and organellar) of the maternal parent of the seed may thus be examined by analyzing the maternal DNA obtained from the seed coat surface of a seed that was produced by the said maternal parent plant. This may e.g. be done for the purpose of confirming that the individual seeds belonging to a batch of seeds were produced by genetically the same mother plant, or to detect different maternal origins of individual seeds belonging to a batch of seeds. These applications are for example useful in the context of quality control during or after commercial seed production.

The invention thus provides a method for examining the maternal genome of a seed through analyzing maternal DNA, which corresponds to the DNA of the mother plant that produced the seed. Thus, the maternal contribution to the seed's genome may be deduced from the obtained knowledge about the genomic composition of the mother plant, and the mother plant that produced the seed may be identified. In the method of the invention, the maternal DNA of a seed is obtained by contacting a seed with a fluid to dislodge DNA from the seed coat surface, and the DNA thus dislodged from the seed coat surface may subsequently be used for analysis.

The method of the invention does not require any tissue sampling or DNA extraction method, apart from the contacting with the fluid. Also, no special equipment is needed, apart from the DNA analysis equipment. Therefore the presented method is highly efficient and cost effective.

Depending on the DNA assay method that is used, results may be obtained within 20 minutes, starting from the dry seeds, which makes this an extremely fast procedure for obtaining genetic information from a seed and its maternal origin. Importantly, germination of the seeds is not required to work this invention, and this method may be applied on all plant species having a seed coat, without major adaptations to the protocol. Optimisation of the method for different plant species merely involves small changes in the agitation frequency and/or duration that may be needed to dislodge seed coat DNA into the surrounding liquid medium. This method thus enables the very rapid sampling of DNA from the maternal parent of a seed or of the maternal parent(s) of a population of seeds, which may subsequently be analysed using standard DNA analysis methods.

The method of the invention may be up-scaled to a high-throughput setup, which enables the simultaneous isolation of maternal DNA from large numbers of individual seeds in parallel, or from large numbers of individual seed batches. In this setting the method may be automated or robotised, leading to a very significant cost and labour reduction in all steps of the DNA isolation procedure from plant populations. The container containing the fluid in which DNA from the seed coat is dislodged may be part of a multi-tube format or of a micro- or macroplate format, which is compatible with an automated system for high-throughput analysis of maternal DNA in large plant populations. In such an automated setup many seeds may be analysed in parallel. This method is therefore particularly suited for screening large populations of seeds, and it may be readily applied in e.g. quality control and plant breeding.

According to a further aspect thereof the invention thus also relates to a high throughput DNA analysis system for large plant populations, which may comprise an array of containers arranged for contacting one or more seeds with a fluid to dislodge DNA from the seed coat surface, and means for analyzing the DNA thus dislodged from the seed coat surface. The system is in particular suitable for analyzing maternal DNA.

In a high-throughput setup, multiple containers may be aligned in a row, or arranged in a multiple-well plate-format, and in each of these containers a seed may be contacted with the fluid.

The automation of the method of the invention may comprise the automated steps of contacting individual seeds with a fluid, which sits in a container, optionally the agitation of the fluid to facilitate the dislodgement of the seed coat DNA, the removal of the seed from the fluid, and optionally the drying of the seed. Optionally, the same automated setup could also carry out the step of collecting the fluid containing the seed coat DNA for further analysis, and optionally also the actual molecular analysis of the said DNA. The seeds may also be added automatically to the fluid in the containers.

Another high-throughput application of the claimed method may be conceived by contacting more than one seed with a fluid in a single container, and subsequently performing the steps of the method. This application enables the simultaneous analysis of the maternal DNA of multiple seeds, such as a representative sample of a commercial seed batch, or a representative sample of seeds harvested from one mother plant or a group of mother plants. It allows the screening for genetic variation in such a seed batch, with the purpose of e.g. verifying the uniformity and identity of the mother plant or mother plants of the seeds which may comprise in the seed batch, or the identification of seed batches that contain interesting genetic variation (such as in a TILLING population, wherein seeds from one mutated plant or a few mutated plants may be analysed together in a batch, and screened for the presence of specific genetic variation in a genomic region of interest in the mother plant(s). This allows the efficient identification of mutations in mutated plants which may be transmitted to the next generation—i.e. the seeds of the analysed seed batch—even if these mutations occur at a low frequency, and without the need for destructive tissue sampling, as explained in Example 5).

Although the present invention and its advantages have been described in detail, it should be understood that various changes, substitutions and alterations may be made herein without departing from the spirit and scope of the invention as defined in the appended claims.

The present invention will be further illustrated in the following Examples which are given for illustration purposes only and are not intended to limit the invention in any way.

EXAMPLES

Example 1

Obtaining DNA from the Seed Coat of *Brassica oleracea* Seeds

Ninety-two Brassica oleracea seeds were placed in a 96-well plate, after which 50 µl of sterile MilliQ water was added. The plate was sealed, and agitated for 2 minutes in a paint mixer. Subsequently, 5 µl of the water was used immediately for DNA analysis, using a highly sensitive DNA detection assay in a 96-well PCR plate (ABgene). Seed coat DNA obtained with this method may be used for genetic analyses, as will be illustrated below by the other examples. The same procedure may also be used on seeds from other plant species, as will be illustrated below by other examples, and with other DNA analysis techniques and setups. Agitation in a paint mixer did not affect the germination capacity of the seeds.

Example 2

Analysis of Cytoplasmic DNA

This example illustrates that this invention may be used to distinguish between male-sterile (CMS) and fully fertile plants, without the need to first germinate the seeds and grow the plants. This would be required when e.g. a contamination of a hybrid seed batch or of a parental line occurred, and fertile seeds were mistakenly harvested along with the male-sterile seeds. Already in the seed stage this detection is possible, if genetic markers are available to distinguish between male-sterility and male-fertility and if the method of the present invention is used. This approach thus greatly economises plant growth space. Without such a test, all plants would need to be grown to maturity, and examined for male fertility after they started flowering. All fertile plants would need to be identified and removed from the population prior to seed production, which requires the investment of labour and the waste of valuable growth space.

The present invention allows the specific selection of male-sterile seeds (i.e. seeds that will grow into male-sterile plants) from a seed batch, and the breeder may then confidently fill up all his available growth space with confirmed male-sterile individuals. The fact that mitochondria—which harbor the CMS marker in their organellar genome—are typically present in multiple copies in each cell greatly increases the sensitivity of this method. The high copy number of the CMS marker in seed coat DNA samples thus makes it easily detectable.

A batch of broccoli seeds, consisting of eighty-three seeds harbouring a cytoplasmic male sterility (CMS) trait, and five cauliflower seeds that lacked this trait (and that may hence grow out to become fully fertile plants), was used in this experiment. The seeds of this batch were individually placed in the wells of a "screenmate tube" plate, 50 µl sterile MilliQ water was added to each well, and the procedure as described in Example 1 was followed. The seeds were incubated for 3 minutes, and subsequently agitated at 600 rpm in a paint mixer, for 20 seconds. Subsequent DNA analysis by PCR resulted in the correct identification of the five fertile seeds within this seed batch of 88 seeds.

FIG. 1 illustrates the results of this experiment: along with two control samples for absence of the CMS marker, the five cauliflower seed samples that lacked the CMS marker may be clearly distinguished from the other seeds of the batch. This approach allows the detection of "contaminating" fertile progeny among a batch of "male sterile" seeds.

Example 3

Obtaining Genetic Information about the Mother Plant of a Seed

This example demonstrates that the DNA that is obtained with the claimed method is purely maternal in origin. Brassica seeds were first subjected to the non-destructive DNA-isolation procedure of the present invention as outlined in Example 1, and subsequently to a conventional, destructive DNA extraction method, for which latter purpose the seeds were homogenised. A nuclear DNA-marker was tested on the DNA that had been obtained from the same seeds with the two different methods. For this specific marker it was known that the hybrid seeds' father plant was homozygous for the A allele, and that the hybrid seeds' mother plant was homozygous for the B allele. The nuclear genome of the seeds that were analysed in this assay was thus in all cases heterozygous (AB) for this specific marker.

Figure 2:
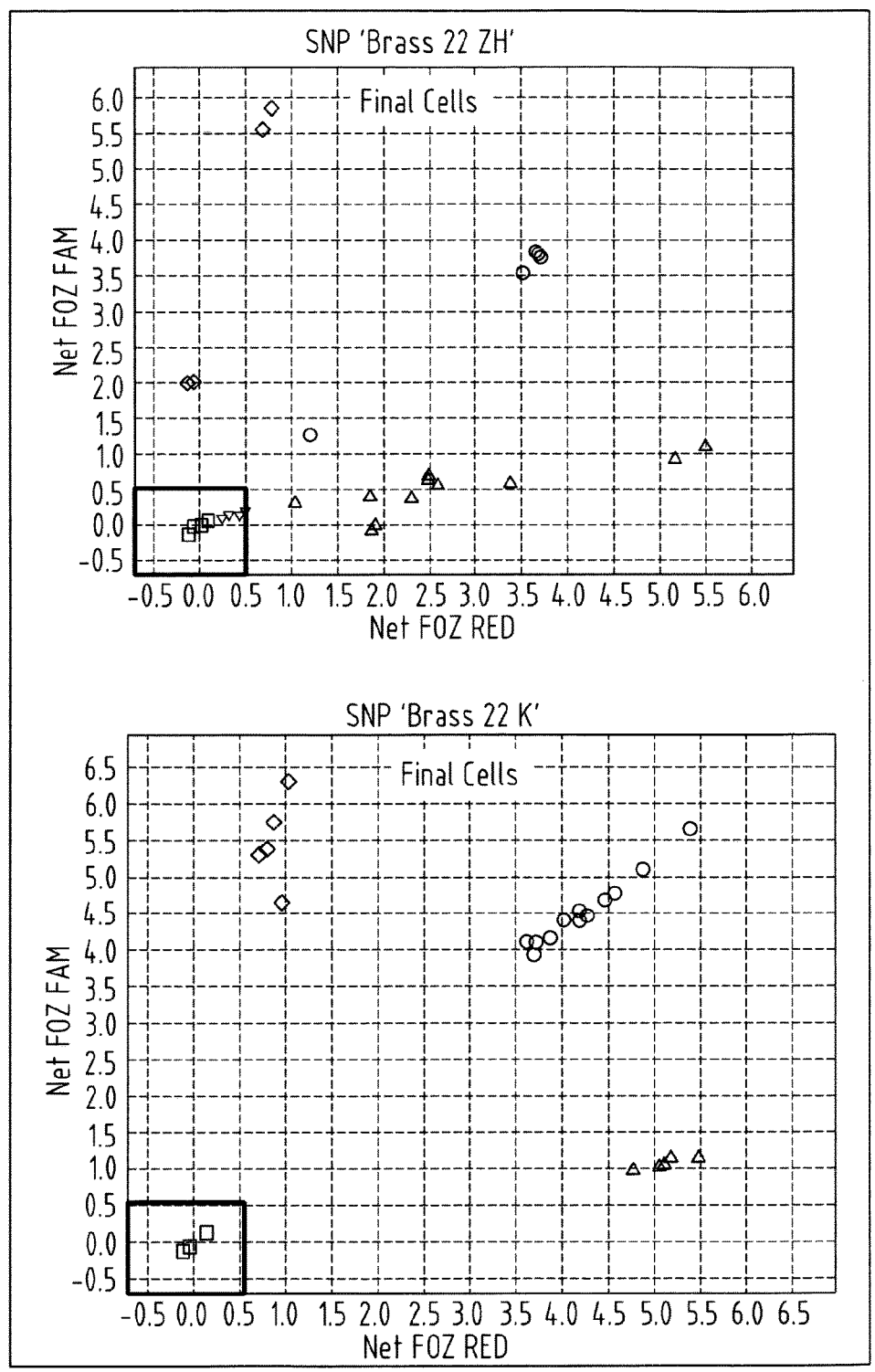
FIG. 2 shows in the upper panel the marker scores (fluorescence plot) obtained for a nuclear marker, when tested on DNA obtained with the method of the present invention. Except for the control samples for homozygous AA (green ◇, paternal allele) and heterozygous AB (blue ○) scores, all samples scored homozygous BB (red □, maternal allele), which confirms that only the maternal allele of the nuclear marker was detectable in the DNA sample obtained with the method of the invention. In comparison, the lower panel of FIG. 2 shows the result obtained for the same nuclear marker, when tested on genomic DNA that was extracted from the same seeds with a standard, destructive DNA isolation method. This isolation clearly resulted in the isolation of hybrid DNA, as in this test all experimental samples scored heterozygous (blue ○) for the nuclear marker.

FIG. 2 shows in the upper panel the marker scores (fluorescence plot) obtained for the tested nuclear marker, when tested on DNA obtained with the method of the present invention. Except for the control samples for homozygous AA (green ◇) and heterozygous AB (blue ○) scores, all samples scored homozygous BB (red □), which confirms that only the maternal alleles of the nuclear marker were detectable in the DNA sample obtained with the method of the invention.

In comparison, the lower panel of FIG. 2 shows the result obtained for the same nuclear marker, when tested on genomic DNA that was extracted with a standard, destructive DNA isolation method from the same seeds. This isolation clearly resulted in the isolation of hybrid DNA, as in this test all experimental samples scored heterozygous (blue ○) for the nuclear marker.

Example 4

Detection of Genetic Contamination in a Seed Batch

Into a batch of 89 hybrid sweet pepper seeds (*Capsicum annuum*), produced on a male-sterile mother line (harbouring a GMS trait) with pollen obtained from a specific father line, four seeds produced by a genetically different mother line were mixed (to simulate a background degree of accidental contamination of the hybrid seed batch with seeds from a different variety or mother line). The seeds were placed individually into the wells of a 96-well plate, and the procedure of Example 1 was applied.

Subsequently aliquots of the liquid were immediately analysed by PCR, to detect the presence or absence of various genetic markers that allowed differentiation between different sweet pepper mother lines that are often used at the same time in the same growth facility. All 89 hybrid seeds produced by the correct mother line scored positive for its corresponding marker, while the four "contaminating" seeds scored negative for this marker. However, these four seeds scored positive for another marker, while the other 89 seeds scored negative for that marker. This assay thus resulted in the unambiguous detection of the four "contaminating" seeds of another mother line that did not correspond to the desired hybrid genotype.

To further speed up the detection of "contaminating" mother lines in the production facility, it is also possible to combine the liquid from all 93 seeds (or to extract seed coat DNA from this seed batch as a whole), and to test this combined fluid for genetic markers that are specific for each of the mother lines that were used in the production facility. In the current example, this approach would lead to the positive detection of two distinct maternal origins in this seed batch, which would indicate that a certain level of contamination was present, caused by the presence of seeds from another mother line than the one that was intended to be used to produce that specific hybrid variety. This simple test would thus result in a quick warning that the entire seed batch from which the sample was taken should be analysed more carefully.

Example 5

Genetic Analysis of Large Mutagenised Populations

In the field of plant breeding the application of reverse genetics is becomes increasingly widespread. Reverse genetics relates to an approach in which genes are isolated and their function is determined by modifying their primary structure and/or expression. With the current increase in knowledge on gene function, especially in model systems such as *Arabidopsis thaliana*, rice and maize, reverse genetics approaches in crop systems currently gain in efficacy.

In order to determine the presence of specific genes or alleles, numerous diagnostic DNA tools are available and known to the person skilled in the art. The cost of screening plant populations is largely determined by the labour and space required to grow and sample individual plants of the population under investigation, and to isolate DNA from these samples. In case a population is available as individual seed samples, representing the genetic variation residing within individual plants of the population under investigation, significant labour has already been invested in harvesting seeds plant by plant as related individuals in families. Once tissue of the plant has been sampled, after germinating or growing it, the preferred plant has to be used or grown to maturity immediately to determine its genetic value and identity. This process, once set in motion, cannot be terminated or reversed. Failure to timely investigate the available phenotypic and genotypic information in the population may result in the irreversible loss of interesting genetic combinations or of interesting alleles.

For example, when a population of plants or seeds has been subjected to mutagenesis (using mutation-inducing protocols known to the skilled person), first an M0 population is obtained. Depending on the specific cell(s) that were mutagenised by the mostly random means for mutagenesis (such as ethyl methane sulfonate), the M0 plants are typically chimeric. This means that the genetic constitution of different parts of an M0 plant is not identical, and that in some sectors of the plant the cells may harbor a mutation of interest, while in other sectors of the same plant the cells harbor the wildtype allele for that gene. The size of the sectors depends on the developmental fate of the cells that were originally mutagenised, e.g. in a seed that was subjected to a mutagenic agent, and on the function of the cell lineages that are produced throughout plant development from the said mutagenised cell or cells (or sector or sectors of cells).

Typically only mutations that are present in a plant's germ line (i.e. the cell lineages that ultimately give rise to the formation of pollen grains and/or egg cells) may be transmitted to the next generation. A random mutagenesis approach often leads to M0 plants of which some flowers produce seeds that harbor a desired mutation, while other flowers of the same plant produce seeds that do not harbor the said mutation. Theoretically it would be possible to examine this variation in detail and to distinguish between both types of flowers, but considering the typically very large size of mutant populations and the required investment of time and labour into such a task, this is not something a researcher would contemplate.

Typically, seeds from M0 plants are harvested from each individual plant, without thereby distinguishing between the individual fruits of that plant. Those seeds—termed M1 seeds—are thus in many cases (in which the germ line of the M0 plant was chimeric) not homogenous for the desired mutation. In cases wherein the mutagenised sector was rather restricted to the germ line of only one or few flowers, one may thus very easily overlook the presence of the mutation, as the M1 seeds carrying that mutation are relatively rare among the entire M1 seed batch harvested from the same M0 plant. A researcher often does not have sufficient growth space at his disposal to germinate, grow and analyze all M1 seeds from every single M0 plant of his entire mutagenised population, and mutations that are present in only a relatively small percentage of the M1 seeds may not be observed when random small seed samples of the progeny of each M0 plant are analysed.

Using the method of the present invention, it is feasible to quickly analyze a seed batch for the presence of a desired mutation in the mother plant or mother plants that produced the said seed batch. The method of the present invention may be used on M1 seeds, but also on M2 seeds, or on seeds from later generations. Once the presence of a desired mutation in a given seed batch has been detected, all seeds produced by that mother plant (or those mother plants) may be analysed on an individual basis, using the non-destructive method of the invention, and subsequently these seeds may still be sown and germinated.

This procedure will allow the identification of individual seeds of which the mother harboured the said mutation, even if they are rare among the bulk of seeds produced by the said plant or plants. This strategy greatly optimises the efficiency of e.g. TILLING approaches, wherein the researcher focuses on mutations in a predefined region of the genome. The rapid identification of individual, non-germinated seeds that have a high chance of harbouring a desired mutation omits the necessity for growing all M1 seeds, or all M2 seeds, or all seeds from any subsequent generation, as it allows the selective growing of only those individuals of the population of which the mother plant harbours a mutation of interest. This saves growth space, labour and time.

Alternatively, if the M2 generation of a mutagenised plant population is available, application of the method of the present invention allows a very similar approach. An M2 population offers the advantages that chimerism is no longer present, and that mutations may be present in a homozygous state, which facilitates the analysis of the phenotypical effects of said mutations, even if they are recessive in nature.

It is then possible to e.g. screen for the presence of a desired mutation in every individual M2 seed pool or seed batch (wherein each seed pool is either harvested from a single M1 plant or from a group of individual M1 plants), and thus to identify M2 seed batches that are of particular interest, i.e. produced by a mother plant harbouring a mutation in a genomic region of interest and/or a specific desired mutation. Instead of germinating the seeds from every M2 seed batch and subsequently isolating DNA from parts of seedlings or mature plants (such as leaf discs) with existing destructive DNA-isolation protocols, one may then choose to only germinate the seeds of preselected batches, in which the mutation of interest has been detected in the maternal genome.

In this manner it is no longer necessary to grow many thousands of plants that lack the desired genetic variation, and the researcher may choose to specifically grow plants in which he knows that the chance of detecting the desired mutation is significant, as said mutation had been previously shown to be present in the maternal DNA of the selected seed batch. When an M1 plant carrying the mutation in a heterozygous state had been selfed to obtain the M2 seeds, the mutation is expected to be physically present in the genome of 75% of the said M2 seeds, in the absence of segregation distortion. In case of a dominant mutation, the phenotypical expression thereof will typically be observable in 75% of the M2 plants, and in case of a recessive mutation the phenotypical expression thereof will typically be observable in 25% of the M2 plants, when the M1 plant had been selfed.

This approach greatly reduces the requirement for large growth facilities, as only seeds from selected M2 families are sown, germinated and grown to maturity, instead of all M2 families (which may easily amount to a scale-reduction of the required experimental space with a factor 100 or more).

Also, a researcher could even go one step further in the downscaling of his mutagenesis project, using the method of the present invention. If the M2 seed population consists of multiple M2 seed batches, each of which consists of the pooled seeds of multiple M1 plants (forming an M1 family), the positive identification of a desired mutation will indicate that at least one of the M1 plants that contributed to the said M2 seed batch harboured the desired mutation.

However, because of the mixed origin of the seeds which may comprise in the positive-scoring M2 seed batch it will not be clear which percentage of the individual seeds which may comprise in that seed batch will actually harbor said mutation. If e.g. the seeds of ten M1 plants had been pooled to form the M2 seed batch, and only one of these ten plants harboured the desired mutation, then seeds harbouring the desired mutation will be relatively rare among the seeds of the M2 seed batch (e.g. typically about 75% of 10% of the plants are expected to harbor the mutation, which is about 7.5%, or 3 in 40 plants, and in case of a recessive mutation only 1 of these 3 plants will potentially show a mutant phenotype, i.e. 1 in 40 plants). Thus, after a desired mutation has been detected in the maternal DNA from a representative sample of an M2 seed batch, all individual seeds which may comprise within that said seed batch may subsequently be analysed individually by means of the non-destructive method of the present invention, to precisely identify those individual seeds that were produced by the M1 plant (or plants) in the M1 family that harboured the said mutation.

This high-throughput approach allows the selection from among the mixed M2 seed pool of a subpopulation of M2 seeds, which seeds were produced by an M1 plant (or plants) harbouring the desired mutation. This pre-selection greatly enriches the population of seeds (that is ultimately sown, germinated and grown for analysis) for the presence of the desired mutation. In case of a dominant mutation, the phenotypical expression thereof will typically be observable in 75% of these pre-selected M2 plants, and in case of a recessive mutation the phenotypical expression thereof will typically be observable in 25% of the pre-selected M2 plants, when the M1 plant (being heterozygous for the mutation) had been selfed.

Especially for plant species with large dimensions, which typically require a large growth space per individual plant, this downscaling strategy by using the method of the present invention is very attractive. It may greatly reduce costs and occupied space, and the available space and manpower may be conveniently used for other projects and activities.

Example 6

Improvement of the Efficiency of Reverse Progeny Mapping

The Reverse Progeny Mapping method, as described in European patent application EP2366792, may be further improved and rendered more efficient when combining it with the method of the present invention. Reverse Progeny Mapping is an invention which takes advantage of the fact that SDR-0 plants, produced through second division restitution (SDR, the omission of the second meiotic division), have residual heterozygosity in their genome, in contrast to double haploid (DH) plants, which are fully homozygous. This residual heterozygosity is due to the fact that recombination (chromosomal cross-over) has occurred during the first meiotic division. SDR-0 plants produce SDR-1 seeds, and in this SDR-1 generation a segregation may be observed for any trait that resided in a chromosomal region for which the SDR-0 mother plant was heterozygous. When a phenotype of interest is observed to segregate in SDR-1 plants obtained from a specific SDR-0 plant, the genome of that SDR-0 plant may be genotyped in order to identify which precise chromosomal regions were heterozygous. Such heterozygous regions are candidate regions for the genomic location of the trait of interest, and in this manner the trait may be mapped to the genome, and may the underlying genomic sequences be identified. However, a requirement for this method is the collection and storage of genomic DNA of all SDR-0 plants from which SDR-1 seeds will be harvested for subsequent analysis of the SDR-1 plants. Not only does this DNA isolation with conventional methods require labour and time, but it also increases the costs of the experiment.

When applying the method of the present invention to Reverse Progeny Mapping, DNA collection from the SDR-0 plants is no longer needed. Prior to sowing, the SDR-1 seeds may be subjected to the non-destructive method of the invention as described in example 1, to collect maternal DNA from their seed coats. For each individual SDR-1 seed this DNA corresponds to the genomic DNA of the SDR-0 plant that produced it. The genomic basis of any trait that phenotypically segregates in an SDR-1 population may then be searched in the SDR-0 genome, which has been isolated from the SDR-1 seeds' seed coats. Alternatively, the seed coat DNA of only one or a small number of SDR-1 seeds harvested from the same SDR-0 plant may be collected, as this is expected to be identical for all SDR-1 seeds that were produced by the same mother SDR-0 plant. The seed coat DNA of any SDR-1 seed is representative for the maternal DNA of the SDR-0 plant that produced it, and thus also for the seed coat DNA of all SDR-1 seeds harvested from the same SDR-0 plant.

Similarly, the method of the present invention may be used to further improve other methods, such as Near-Reverse Breeding (WO 2006/094773).

The invention is further described by the following numbered paragraphs:

1. Non-destructive method for analysing maternal DNA of a seed, comprising the steps of contacting a seed with a fluid to dislodge DNA from the seed coat surface, and analysing the DNA thus dislodged from the seed coat surface.

2. Method of paragraph 1, wherein the fluid is comprised in a container.

3. Method of paragraph 1 or 2, wherein the seed is immersed in the fluid.

4. Method of paragraph 1 or 2, wherein the seed floats on the fluid.

5. Method of any of the paragraphs 1-4 wherein the seed is agitated within the fluid.

6. Method of paragraph 1 or 2, wherein the seed is rinsed with the fluid.

7. Method of any of the paragraphs 1-6, wherein the fluid is an aqueous solution.

8. Method of any one of the paragraphs 1-7, wherein the fluid is water.

9. Method of any of the paragraphs 1-8, wherein the seed is removed from the fluid, and the fluid is assayed for maternal DNA.

10. Method of any of the paragraphs 1-9, wherein the seed is subsequently dried for storage.

11. Method for examining the maternal genome of the seed through analyzing maternal DNA, wherein the DNA is DNA that is obtained or produced by any one of the methods of paragraphs 1-10.

12. Method of paragraph 11, wherein the DNA is DNA that is obtained or produced by contacting a seed with a fluid to dislodge DNA from the seed coat surface, and analysing the DNA thus dislodged from the seed coat surface.

13. Method of any of the paragraphs 2-10, wherein the container is part of an automated system for high-throughput analysis of maternal DNA in large plant populations.

14. Method of any of the paragraphs 1-13, wherein more than one seed is contacted with a fluid in a container.

15. High throughput DNA analysis system for large plant populations, comprising an array of containers arranged for contacting one or more seeds with a fluid to dislodge DNA from the seed coat surface, and means for analysing the DNA thus dislodged from the seed coat surface.

* * *

Having thus described in detail preferred embodiments of the present invention, it is to be understood that the invention defined by the above paragraphs is not to be limited to particular details set forth in the above description as many apparent variations thereof are possible without departing from the spirit or scope of the present invention.

What is claimed is:

1. A method for analyzing maternal DNA of a seed, comprising the steps of
   contacting a seed with a fluid to dislodge maternal DNA present on the outer surface of the seed coat, wherein the seed is not subjected to crushing, grinding, or destruction and the seed coat is not removed from the seed; and
   directly analyzing the maternal DNA present in the fluid.

2. The method as claimed in claim 1, wherein the fluid is comprised in a container.

3. The method as claimed in claim 2, wherein the container is part of an automated system for high-throughput analysis of maternal DNA in large plant populations.

4. The method as claimed in claim 1, wherein the seed is immersed in the fluid.

5. The method as claimed in claim 1, wherein the seed floats on the fluid.

6. The method as claimed in claim 1, wherein the seed is agitated within the fluid.

7. The method as claimed in claim 1, wherein the seed is rinsed with the fluid.

8. The method as claimed in claim 1, wherein the fluid is an aqueous solution.

9. The method as claimed in claim 1, wherein the fluid is water.

10. The method as claimed in claim 1, wherein the seed is removed from the fluid, and the fluid is assayed for maternal DNA.

11. The method as claimed in claim 1, wherein the seed is subsequently dried for storage.

12. The method as claimed in claim 1, wherein more than one seed is contacted with a fluid in a container.

13. The method as claimed in claim 1, wherein the fluid is comprised in an array of containers, and the array of containers are part of an automated system for high-throughput analysis of maternal DNA in large plant populations.

* * * * *